US012678300B2

(12) United States Patent (10) Patent No.: US 12,678,300 B2
Foley et al. (45) Date of Patent: Jul. 14, 2026

(54) TELEMETRY TRIAL FOR DIGITAL IMPLANT

(71) Applicant: Warsaw Orthopedic, Inc., Warsaw, IN (US)

(72) Inventors: Kevin T. Foley, Germantown, TN (US); Steven D. Glassman, Louisville, KY (US); Adam D. Glaser, Collierville, TN (US); Newton H. Metcalf, Jr., Memphis, TN (US); Jerald L. Redmond, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 19/272,557

(22) Filed: Jul. 17, 2025

(65) Prior Publication Data

US 2026/0090899 A1 Apr. 2, 2026

Related U.S. Application Data

(60) Provisional application No. 63/700,995, filed on Sep. 30, 2024.

(51) Int. Cl.
*A61B 17/70* (2006.01)
*A61F 2/46* (2006.01)
*A61B 17/00* (2006.01)

(52) U.S. Cl.
CPC .......... *A61F 2/468* (2013.01); *A61B 17/7074* (2013.01); *A61F 2/4684* (2013.01); *A61B 2017/00424* (2013.01); *A61B 2017/00455*
(2013.01); *A61B 2017/00681* (2013.01); *A61F 2002/4632* (2013.01); *A61F 2002/4658* (2013.01); *A61F 2002/4662* (2013.01)

(58) Field of Classification Search
CPC ............ A61B 17/7044; A61B 17/7074; A61B 17/7092; A61F 2/468; A61F 2/4684; A61F 2002/4663
See application file for complete search history.

(56) References Cited

U.S. PATENT DOCUMENTS

| | | | | |
|---|---|---|---|---|
| RE42,525 E | * | 7/2011 | Simonson | A61M 5/46 604/117 |
| 8,672,948 B2 | * | 3/2014 | Lemaitre | A61B 90/06 33/512 |
| 9,084,688 B2 | * | 7/2015 | Hes | A61F 2/4657 |
| 2007/0079517 A1 | * | 4/2007 | Augostino | A61F 2/4405 33/512 |
| 2007/0237307 A1 | * | 10/2007 | Suddaby | A61B 90/39 378/205 |

(Continued)

*Primary Examiner* — Nicholas W Woodall
(74) *Attorney, Agent, or Firm* — FOX ROTHSCHILD LLP

(57) ABSTRACT

Devices and methods for trial-fitting smart medical implants are disclosed. A trial fitting device for a smart implant includes a handle, a shaft extending from the handle, a head portion attached to the shaft such that the head portion rotates with the shaft, and a rotational indicator disposed on the shaft and/or the handle, the rotational indicator configured to indicate a rotational orientation of the head portion. The trial fitting device further includes a telemetry gauge disposed on the shaft and/or the handle, the telemetry gauge configured to indicate a threshold distance from the head portion.

20 Claims, 5 Drawing Sheets

(56) References Cited

U.S. PATENT DOCUMENTS

| | | | |
|---|---|---|---|
| 2008/0287959 A1* | 11/2008 | Quest | A61F 2/4405 |
| | | | 606/87 |
| 2009/0177195 A1* | 7/2009 | Rawles | A61F 2/4684 |
| | | | 606/53 |
| 2017/0196508 A1* | 7/2017 | Hunter | A61B 5/4566 |
| 2017/0239067 A1* | 8/2017 | Nino | A61F 2/447 |
| 2018/0214283 A1* | 8/2018 | Johannaber | A61F 2/3859 |
| 2018/0256277 A1* | 9/2018 | Garvey | A61B 17/1659 |
| 2019/0105183 A1* | 4/2019 | Adamo | A61B 17/1633 |
| 2019/0117276 A1* | 4/2019 | Dhupar | A61B 90/30 |
| 2019/0240045 A1* | 8/2019 | Couture | A61F 2/4684 |
| 2020/0146697 A1* | 5/2020 | Giri | A61F 2/447 |
| 2021/0153857 A1 | 5/2021 | Hill et al. | |
| 2021/0346176 A1* | 11/2021 | MacMillan | A61F 2/4684 |
| 2022/0265256 A1 | 8/2022 | Villamil et al. | |
| 2024/0115396 A1* | 4/2024 | Loke | A61B 17/1757 |
| 2024/0245529 A1* | 7/2024 | Cowan | A61F 2/4611 |

* cited by examiner

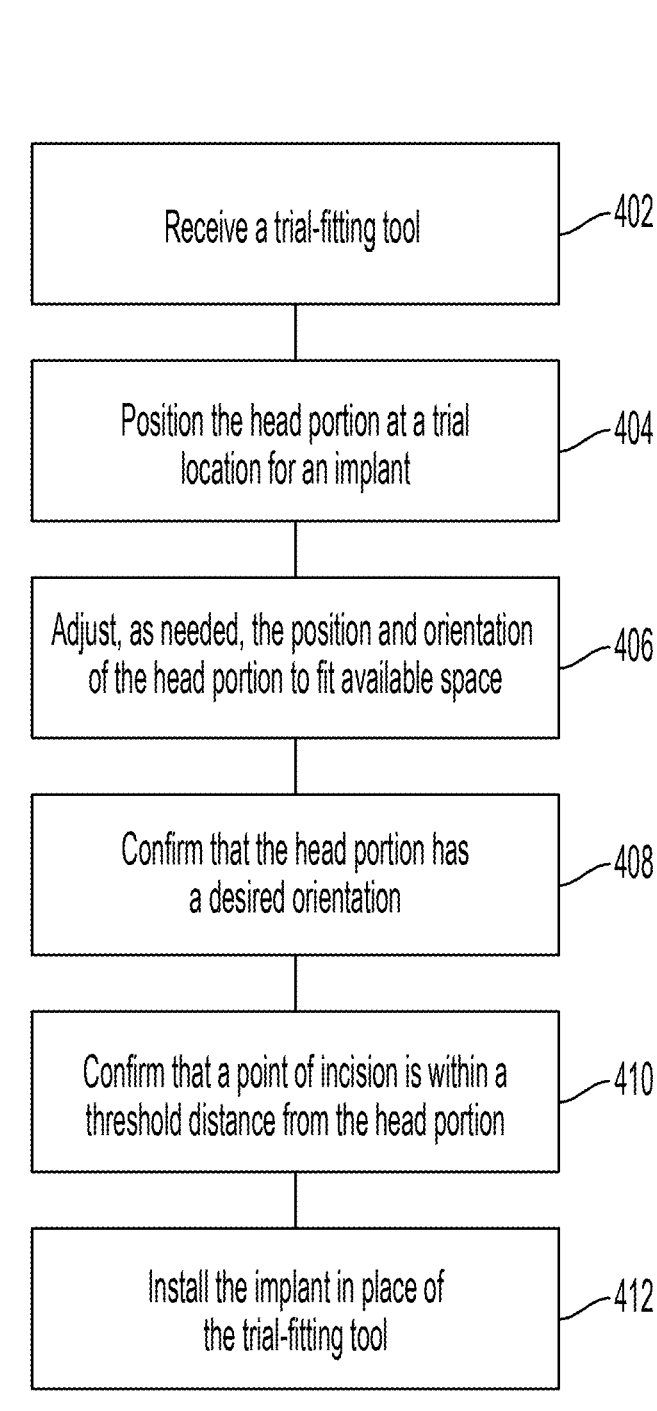

400

Receive a trial-fitting tool — 402

Position the head portion at a trial location for an implant — 404

Adjust, as needed, the position and orientation of the head portion to fit available space — 406

Confirm that the head portion has a desired orientation — 408

Confirm that a point of incision is within a threshold distance from the head portion — 410

Install the implant in place of the trial-fitting tool — 412

FIG. 4

TELEMETRY TRIAL FOR DIGITAL IMPLANT

CROSS-REFERENCE TO RELATED APPLICATION

This application claims the benefit of and priority to U.S. Provisional Patent Application No. 63/700,995 filed Sep. 30, 2024, the entire disclosure of which is incorporated by reference herein.

BACKGROUND

The present disclosure generally relates to devices and methods for trial-fitting implants.

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of longitudinal members, such as spinal rods. Longitudinal members may be attached to the exterior of two or more vertebral members to assist with the treatment of a spinal disorder. Longitudinal members may provide a stable, rigid column that helps bones to fuse, and may redirect forces over a wider area away from a damaged or defective region. Also, rigid longitudinal members may help in spinal alignment.

Screw assemblies may be used to connect a longitudinal member to a vertebral member. A screw assembly may include a pedicle screw, hook, or other connector, among other components. A pedicle screw can be placed in, above and/or below vertebral members that were fused, and a longitudinal member can be used to connect the pedicle screws which inhibits or controls movement. A set screw can be used to secure the connection of a longitudinal member to a pedicle screw, hook or other connector. Implants may include one or more sensors for monitoring aspects of the treatment and transmitting sensor data to an external reader. However, implants placed in deep tissue may have insufficient telemetry performance due to signal attenuation. Furthermore, the position and/or orientation of the implant may be constrained by spinal anatomy, adjacent implants, or other factors. Therefore, there is a need for an integrated tool that provides for both (a) trial fitting an implant and (b) providing an indication of expected telemetry performance in the trial position and orientation.

This document describes methods and systems that are directed to addressing the problems described above, and/or other issues.

SUMMARY

The techniques of this disclosure generally relate to devices and methods for trial-fitting implants. Issues associated with prior solutions are addressed by the subject matter of the independent claims included in this document. Additional advantageous aspects are included in the dependent claims.

In one aspect, the present disclosure provides a device for trial-fitting a smart implant. The device includes a handle, a shaft extending from the handle, a head portion attached to the shaft such that the head portion rotates with the shaft, and a rotational indicator disposed on the shaft and/or the handle, the rotational indicator configured to indicate a rotational orientation of the head portion. The trial fitting device further includes a telemetry gauge disposed on the shaft and/or the handle, the telemetry gauge configured to indicate a threshold distance from the head portion.

Implementations of the disclosure may include one or more of the following optional features. In some examples, the head portion is shaped and dimensioned to correspond with a smart implant. The head portion may include a visual cue of where a longitudinal rod would interface with the smart implant. In some examples, the telemetry gauge is configured to indicate a depth of tissue that permits effective telemetry from a smart implant in the position and orientation of the head portion. The telemetry gauge may be configured to indicate a range of distances indicating a range of tissue depths that permit effective telemetry, the range of distances based on a parameter of the tissue. In some examples, the trial fitting device further includes a transmitter disposed in the head portion, the transmitter configured to transmit a test signal. The trial fitting device may further include a control configured to cause the transmitter to transmit the test signal. The transmitter may be configured to transmit the test signal at one of at least two different strengths. In some examples, the handle and the shaft share a longitudinal axis. The handle may include an ergonomic grip. The rotational indicator may be etched into the handle. In some examples, the head portion is shaped and dimensioned to correspond with an interbody device.

In one aspect, the present disclosure provides a method of trial-fitting an implant. The method includes receiving a trial-fitting tool, the trial-fitting tool including a handle, a shaft extending from the handle, a head portion attached to the shaft such that the head portion rotates with the shaft, the head portion shaped and dimensioned to correspond with a smart implant, and a rotational indicator disposed on the shaft and/or the handle, the rotational indicator configured to indicate a rotational orientation of the head portion. The trial-fitting tool further includes a telemetry gauge disposed on the shaft and/or the handle, the telemetry gauge configured to indicate a threshold distance from the head portion. The method further includes, using the handle of the trial-fitting tool to position the head portion at a trial location for an implant and adjust, as needed, the position and orientation of the head portion to fit available space. The method further includes confirming, using the rotational indicator, that the head portion has a desired orientation, confirming, using the telemetry gauge, that a point of incision is within the threshold distance from the head portion to the point of incision, and installing the implant in place of the trial-fitting tool.

Implementations of the disclosure may include one or more of the following optional features. In some examples, the method further includes, in response to the head portion not fitting at the trial location, using a trial-fitting tool having a second head portion, the second head portion shaped and dimensioned to correspond with a second smart implant, to position the second head portion at the trial location. Using the trial-fitting tool having the second head portion may include replacing the head portion of the trial-fitting tool with the second head portion. In some examples, the trial-fitting tool further includes a transmitter disposed in the head portion and configured to transmit a test signal, and the method further includes, while the head portion is positioned at the trial location, causing the transmitter to transmit the test signal. In some examples, the method further includes assessing the attenuation characteristics of tissue between the head portion and the telemetry gauge, wherein confirming that the point of incision is within the threshold distance is based on the assessed attenuation characteristics. Positioning the head portion at the trial location may include positioning the head portion by a surgical navigation robot.

BRIEF DESCRIPTION OF THE DRAWINGS

The accompanying drawings are incorporated into this document and form a part of the specification.

FIG. 4 is a flowchart of a method for trial-fitting an implant.

In the drawings, like reference numbers generally indicate identical or similar elements. Additionally, generally, the left-most digit(s) of a reference number identifies the drawing in which the reference number first appears.

DETAILED DESCRIPTION

Figure 1:
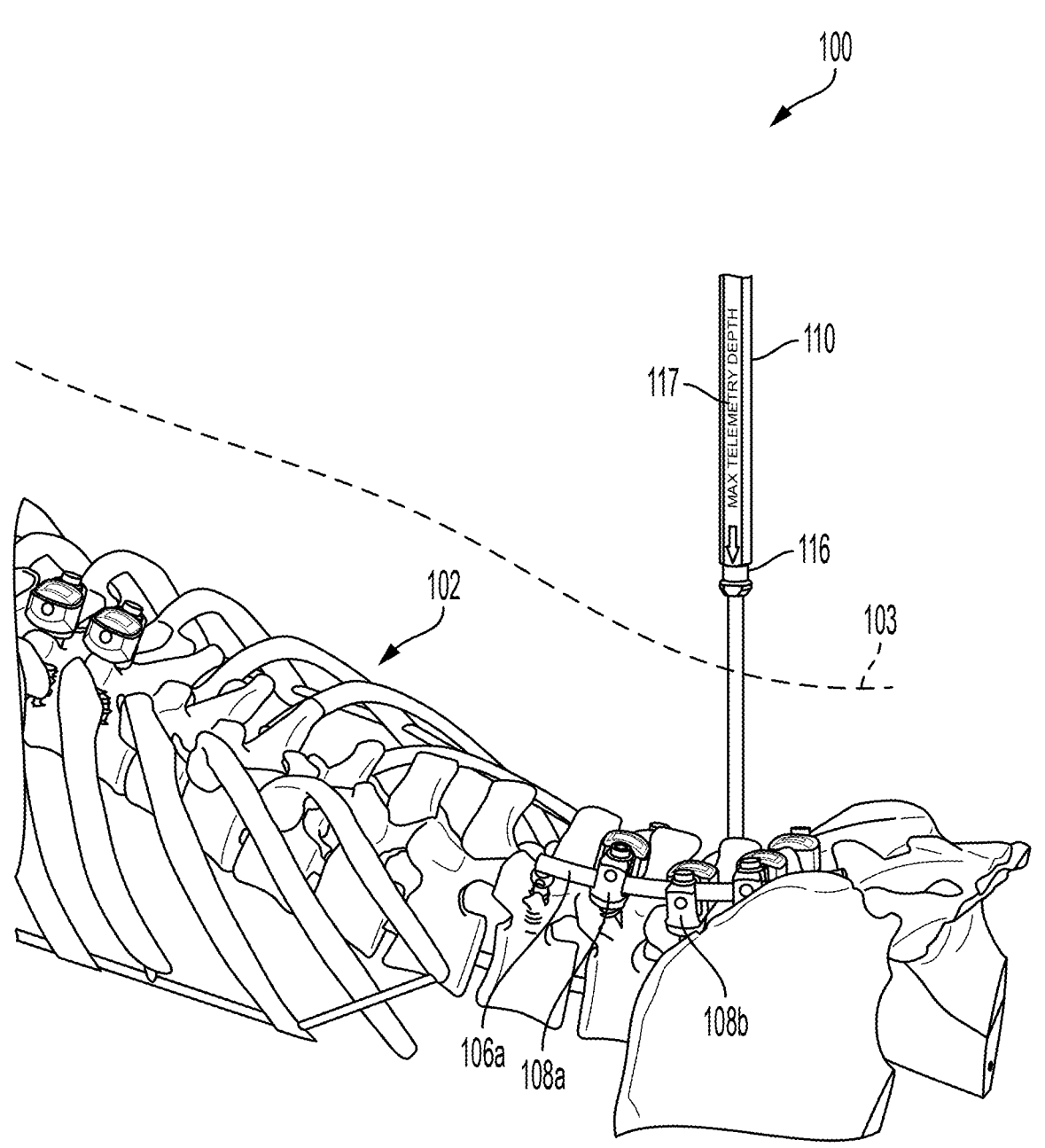
FIG. 1 illustrates an example environment for fitting implants.

The exemplary embodiments of the surgical system and related methods of use disclosed are discussed in terms of medical devices for the treatment of musculoskeletal disorders and more particularly, in terms of a vertebral fixation screws, including for example pedicle screws, as well as hooks, cross connectors, offset connectors and related systems for use during various spinal procedures or other orthopedic procedures. These may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. Exemplary prior art devices that may be modified to include the various embodiments of load sensing systems include, for example, U.S. Pat. Nos. 6,485,491 and 8,057,519, incorporated herein by reference in their entirety.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other and are not necessarily "superior" and "inferior." Generally, similar spatial references of different aspects or components indicate similar spatial orientation and/or positioning, i.e., that each "first end" is situated on or directed towards the same end of the device.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

The following discussion includes a description of an integrated tool that provides for both (a) trial fitting an implant and (b) providing an indication of expected telemetry performance of an implant in the trial position/orientation in accordance with the principles of the present disclosure. Reference is made in detail to the exemplary embodiments of the present disclosure, which are illustrated in the accompanying figures.

Referring to FIG. 1, an example environment 100 for fitting implants 108 is shown. The environment 100 includes a subject 102 undergoing a procedure. To more clearly illustrate the procedure, FIG. 1 shows only the subject's skeletal system, omitting other tissue. Dashed line 103 represents the outer boundary of the tissue, i.e., the subject's skin. As shown, the subject 102 is receiving treatment to the lumbar region of the spine. In particular, FIG. 1 shows a spinal rod 106*a* on the left side of the subject's spine connecting one or more implants (e.g., implants 108*a*, 108*b*). As shown, the implants include pedicle screws. Other examples of implants within the scope of the disclosure include interbody "cages." FIG. 1 further illustrates the process of trial fitting of at least one additional implant 108 on the right side of the subject's spine. For example, a surgeon may be installing a second spinal rod 106*b* (not shown) and connecting the second spinal rod 106*b* to one or more additional implants 108. Before installing the additional implants 108, the surgeon may first use trial fitting tool 110 to assess various positions and/or orientations of the implant 108, e.g., to check for interference with or other constraints imposed by the subject's anatomy. That is, the surgeon may check that there is adequate room for the implant 108 in its required orientation. Furthermore, if the additional implants 108 are configured to provide telemetry, the trial fitting tool 110 may also provide an indication of expected telemetry performance of the implants 108 in their trial position/orientation. As shown the trial fitting tool 110 includes a tissue-depth gauge 116 which indicates the maximum depth of tissue through which the implant 108 is expected to be able to transmit data to an external reader device 502 (FIG. 5), without undue signal attenuation due to the tissue.

Figures 2A, 2B:
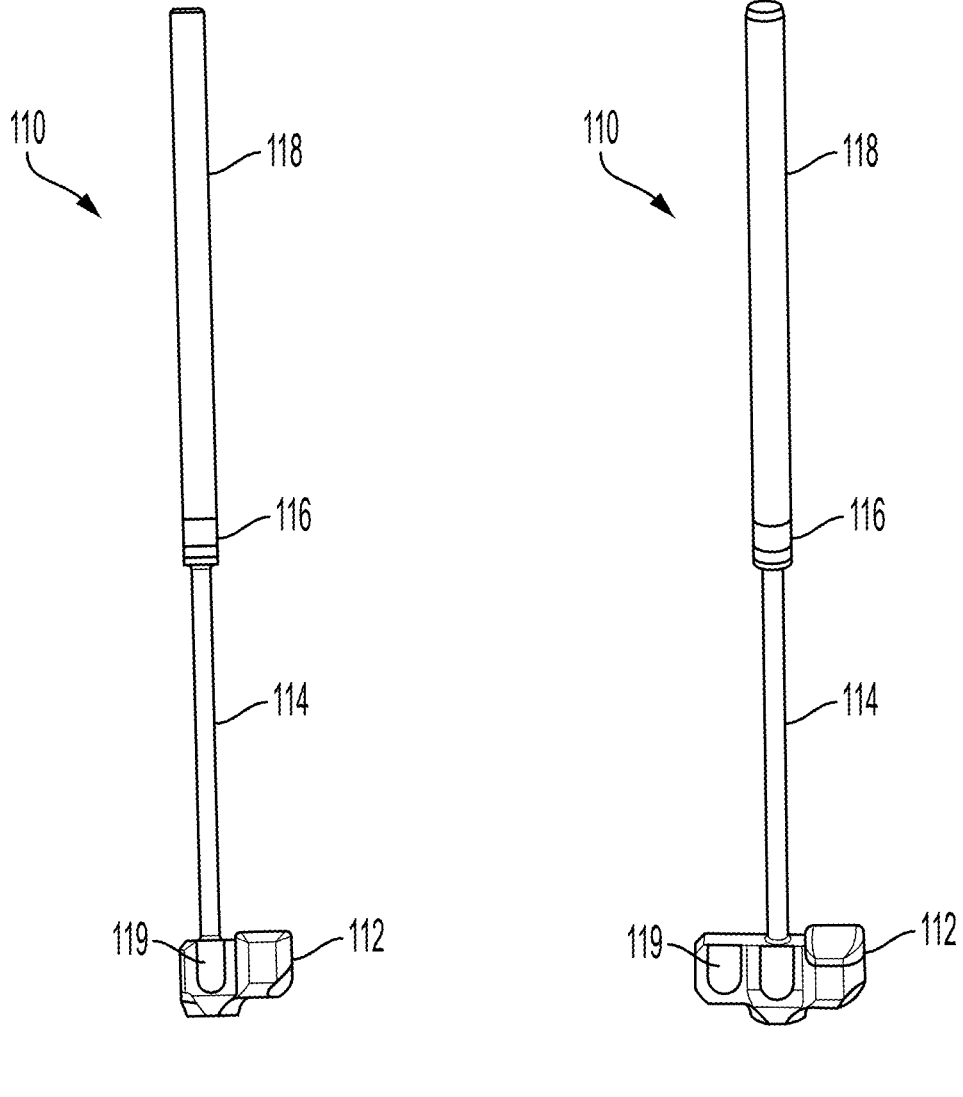
FIGS. 2A and 2B illustrate example embodiments of a trial-fitting tool.

FIG. 2A illustrates an example embodiment of a trial-fitting tool 110. The tool 110 includes a head portion 112 that is configured to have a shape and dimensions that sufficiently correspond with the intended implant 108 that the head portion 112 is an effective gauge of available space for the implant 108. In some embodiments, the dimensions of the head portion 112 are slightly larger than the corresponding implant 108 to assure adequate clearance with nearby anatomy or other source of interference. FIG. 2B illustrates another example embodiment of a trial-fitting tool 110. The embodiment of FIG. 2B differs from the embodiment of FIG. 2A in that the head portion 112 has shapes and dimensions that correspond to a different implant 108 than the embodiment of FIG. 2A. Other shapes and dimensions of implants 108 are also within the scope of this disclosure, including interbody "cages," and any other implant capable of providing telemetry. For example, in the case of interbody devices, the head portion 112 has a shape and dimensions that correspond to the interbody device.

Furthermore, the head portion 112 may include one or more registration features. For example, the implant 108 that corresponds to the head portion 112 may be configured to attach to a pedicle screw or other anchoring device. The head portion 112 may include a feature configured to engage with the anchoring device during the trial fit to more precisely position the head portion 112 in the same location as the corresponding implant 108.

The head portion 112 is attached to a shaft 114 such that the head portion 112 rotates with the shaft 114. Using the shaft 114, the surgeon is able to adjust the position and orientation of the head portion 112 while performing trial fitting. In some examples, the head portion 112 is removable from the shaft 114 and may be interchanged with other head portions 112. A trial fitting kit may include multiple head portions 112, each of which corresponds to a different size or shape implant 108. The surgeon may use such a trial fitting kit to assess which types of implants 108 are suitable for use. That is, the surgeon may assess which types of implants 108 have adequate clearance with respect to the subject's anatomy. In other embodiments, the head portion 112 is permanently affixed to the shaft 114. In these embodiments, a trial-fitting kit may include multiple trial-fitting tools 110, each of which corresponds to a different particular implant 108.

Referring back to FIG. 1, the handle 118 of the tool 110 may include labels, instructions, or other text and/or shapes or symbols that act as a rotational position indicator 117. The surgeon may use the text and/or symbols as indicator 117 of the rotational orientation of the tool 110 and, thus, the head portion 112. This feature may be particularly useful when the head portion 112 is not visible during the trial fit, such as during minimally invasive procedures. In other embodiments, a rotational indicator 117 is disposed on the shaft 114, rather than (or in addition to) the handle 118. The indicator 117 may be as simple as a line etched in the shaft 114 which indicates a reference direction of the head portion 112, such as the direction toward a longitudinal rod 106 of the construct. The head portion 112 itself may also include a visual cue 119 of its orientation. In circumstances where the head portion 112 is visible during the trial fit, the visual cue 119 may provide the clearest indication of the orientation of the head portion 112 (and thus, the ultimate implant 108). In some examples, the visual cue 119 is an indication of where a longitudinal rod 106 would interface with an implant 108. Thus, the visual cue 119 can help align the head portion 112 with other components of a construct, e.g., the rod slots of adjacent spinal-level implants 108.

In the embodiment of FIGS. 2A and 2B, the shaft 114 is shown as substantially cylindrical and having a longitudinal axis. As the surgeon rotates the shaft 114 around its longitudinal axis, the head portion 112 also rotates around the longitudinal axis of the shaft 114. In other embodiments, the shaft 114 may have different shapes or configurations that similarly impart rotational force on the head portion 112, allowing the surgeon to predictably position the head portion 112 and to be able to understand the location and orientation of the head portion 112. The shaft 114, in turn, extends from a handle 118. The handle 118 is configured to provide a gripping surface for manipulating the tool 110. The handle 118 may be attached to the shaft 114 so the shaft 114 rotates with the handle 118, similarly to how the head portion 112 rotates with the shaft 114. Some embodiments may also include a ratcheting mechanism between the handle 118 and shaft 114 so that the head portion 112 only rotates in a single direction. As shown in FIGS. 2A and 2B, the handle 118 is generally cylindrical in shape. In other examples, the handle 118 may be polygonal in cross section, e.g., hexagonal, like a typical pencil. The handle 118 may also be ergonomically shaped to provide additional comfort, e.g., by providing a portion having a generous grip area. Furthermore, at least a portion of the handle 118 may include a high-friction surface, such as rubber or a slightly soft composite, to enable a firm grip and/or reduce soft tissue compression during use. In some examples, the trial-fitting tool 110 (e.g., the head portion 112) is canulated to provide for the tool 110 to pass over a Kirschner wire or other temporary fixation device.

The tool 110 may also include one or more depth indicators 116 that represent an upper limit on the amount of tissue that permits effective telemetry from an implant 108 in the position of the head portion 112 to, e.g., an external reader device 502. Modeling and simulation and empirical testing of digital implants 108 in tissue phantom models are used for insight into allowable depth of implantation to maintain telemetry performance and, therefore, positioning the depth indicator 116 on the tool 110. During trial fitting, the surgeon may compare the depth indicator 116 to a suitable reference indicating the extent of the subject's tissue, such as the skin of the subject 102, e.g., at the point of incision. In some embodiments, the depth indicator 116 includes a range of maximum tissue depths that allow for effective telemetry. The range may correspond to, e.g., different types of tissue having different attenuation characteristics. That is, a tissue type that more strongly attenuates the signal may have a smaller maximum depth for effective telemetry. For example, the depth indicator 116 may extend from a first limit for tissue having a relatively larger amount of fat, and a second limit for tissue having a relatively larger amount of muscle. In some embodiments the depth indicator 116 includes a graduated scale and/or may be punctuated by individual indicators 116 each of which correspond to specific objective criteria related to the subject's tissue, such as the subject's Body Mass Index (BMI), gender, etc., and/or subjective criteria, such as an assessment of the subject's tissue, e.g., by the surgeon.

In some examples, the tool 110 is capable of producing a test transmission signal. For example, the head portion 112 may include a transmitter configured to transmit a signal that is representative of the telemetry signal of an implant 108. Furthermore, the head portion 112 may include an antenna having substantially similar characteristics, such as orientation, as the intended implant 108. For example, the test signal may be a pilot tone that is transmitted at a reference power level. The test signal may be actuated by a control switch, push button, or the like, e.g. located on the handle 118 of the tool 110. Using the test signal, the surgeon can empirically assess the strength of the signal outside of the subject's body before committing to install the implant 108 at the trial location/orientation. Based on the assessed strength, the surgeon may decide to trial fit a different position/orientation of the implant 108 and reassess the signal strength until a suitable combination of signal strength and implant position is identified.

In some examples, the transmitter is configured to transmit a signal at one of two or more reference power levels.

For example, during minimally invasive procedures, the surgeon may activate the transmitter at a nominal signal strength. That is, at a signal strength that is substantially similar to the intended implant 108. Because of the small incision, the signal will travel through substantially the same depth of tissue as the signal from the implant 108. During more invasive procedures, such as open-wound procedures, there is a greater opportunity for some or all of the signal to pass through the open incision area, rather than through tissue. Thus, the signal from the trial-fitting tool 110 may be less attenuated than the signal will be from the implant 108. To compensate, the trial-fitting tool 110 may provide for reducing the transmitted signal strength. In some examples, the transmitter of the trial-fitting tool 110 is configurable between two power levels corresponding to minimally invasive procedures vs. open-wound procedures. In some examples, the transmitter is configurable between a greater number of signal strengths, e.g., corresponding to additional types of procedures and corresponding different levels of signal attenuation during the procedure.

Figure 3:
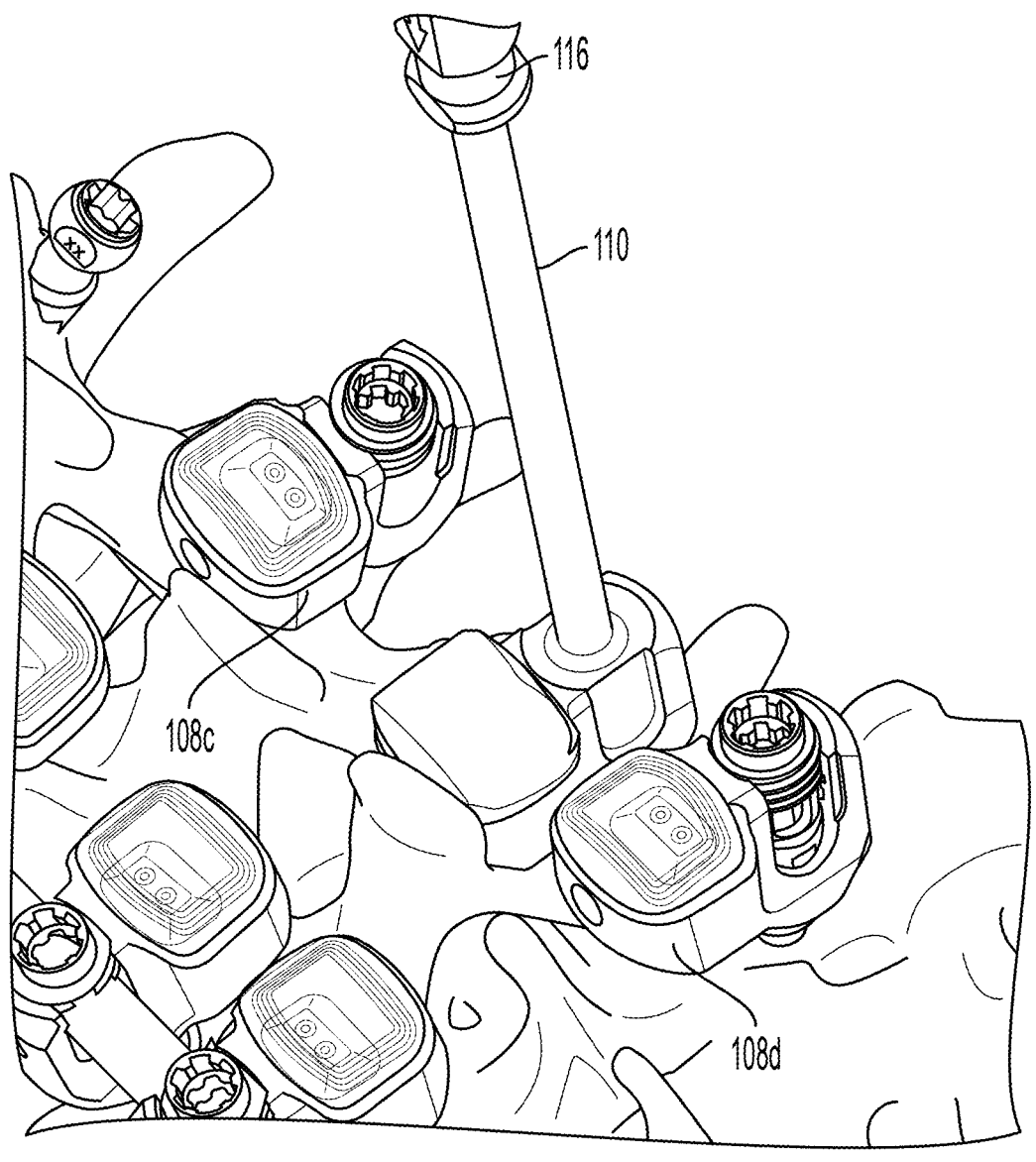
FIG. 3 illustrates a trial fitting.

FIG. 3 illustrates a trial fitting in process. As shown, implants 108*c* and 108*d* have been installed. At this point, the surgeon is trial fitting a potential additional implant 108 between implants 108*c* and 108*d*. Before installing the additional implants 108, the surgeon may use the trial fitting tool 110 to assess both the available space and the expected effectiveness of telemetry from the implant 108. Based on the assessment, the surgeon may install the implant 108 as planned (e.g., if there is adequate space and if the tissue-depth limit of the depth indicator 116 is satisfied). If there is insufficient space to the head portion 112 of the tool 110 in the first trial-fitting position, the surgeon may reposition and/or reorient the head portion 112 of the tool 110 to identify another trial-fitting position that does satisfy the space and tissue-depth criteria. Alternatively, if only the tissue-depth criterion is unmet, the surgeon may opt to install a non-smart implant 108, i.e., and implant 108 that lacks telemetry capability, reserving the smart implants 108 for locations where telemetry will be effective. If only the available-space criterion is unmet, the surgeon may opt to trial-fit an implant 108 having different shape or dimensions. That is, the surgeon may perform a trial fit using a tool 110 having a head portion 112 that corresponds to a different type of implant 108 that may have a better chance of fitting in the available space. As discussed above, the tool 110 that corresponds to the different type of implant 108 may be a separate tool 110, or it may be the same tool 110 fitted with a replacement head portion 112. In either case, if the available-space and tissue-depth criteria are met, the surgeon may opt to install the different type of implant 108.

FIG. 4 shows a flowchart 400 for method of trial fitting. At step 402, the method includes. At step 404, the method includes receive a trial-fitting tool 110. The tool 110 may include some or all of the features described above. At step 404, the method includes positioning the head portion 112 of the trial-fitting tool 110 at a trial location for an intended implant 108. The method may also include orienting the head portion 112, e.g., using the rotational position indicator 117 to be consistent with the expected orientation of the intended implant 108. At step 406, the method includes adjusting, the position and orientation of the head portion 112 to fit within available space. In necessary, at step 406, the method may include using a trial-fitting tool 110 that is associated with a different intended implant 108 (or refitting the tool 110 with a different head portion 112, where the different head 112 portion is associated with the different intended implant 108). The different shape or different dimensions of the different head 112 portion may indicate that there is sufficient space to fit the different intended implant 108

At step 408, the method includes confirming that the head portion 112 has a desired orientation. For example, the surgeon may use the rotational position indicator 117 to confirm that the head portion 112 is aligned with adjacent-level implants 108 (or intended implants 108), and/or a longitudinal rod 106 extending between adjacent-level implants 108. In some examples, at step 408, the method includes confirming, based on a visual cue 119 of the head portion 112, that the head portion 112 has a desired orientation with respect to adjacent-level implants 108. At step 410, the method includes confirming that a point of incision for the procedure is within a threshold distance from the head portion 112. That is, the method includes using the trial-fitting tool 110 to confirm that tissue depth that a signal from the intended implant 108 will pass through is less than a threshold tissue depth for effective telemetry. In some examples, step 410 includes comparing the point of incision to a tissue-depth gauge 116 of the trial-fitting tool 110. In some examples, step 410 includes assessing objective and/or subjective characteristic of the subject's tissue before comparing the point of incision to the tissue-depth gauge 116. The tissue-depth gauge 116 may include a range of depths and/or a graduated scale indicating different tissue depths for different types of tissue. In these cases, step 410 may include comparing the point of incision to the appropriate portion of the tissue-depth gauge 116. In some examples, the method further includes causing the trial-fitting tool 110 to transmit a test signal to confirm that the signal strength outside of the surgical site has adequate strength for effective telemetry.

At step 412, the method includes installing the implant 108 in place of the trial-fitting tool 110. That is, the surgeon may remove the trial-fitting tool 110 and install the intended implant 108 in the location/orientation of the associated head portion 112. The intended implant 108 may be installed using any or several techniques that allow for positioning and orienting the implant 108. In some examples, a surgical navigation system assists placement of the implant 108. In some examples, the position and orientation of the trial-fitting tool 110 is tracked by the surgical navigation system during the trial fit. The surgical navigation system may similarly track the installation of the implant 108. Alternatively, the surgical navigation system may install the implant 108 itself, e.g., using a robotic arm (not shown) or other manipulator capable of navigating to the installation site.

Furthermore, the trial fitting process may be partially or completely performed virtually. For example, a surgical planning program may include a three-dimensional representation of the subject's anatomy. The surgical planning program may also include a virtual trial-fitting tool 110, or at least the head portion 112 of the tool 110. Using a display of the surgical planning program, the surgeon may manipulate and/or orient the virtual head portion 112 into trial positions. The planning program may determine whether there is sufficient space for the intended implant 108 at each trial fit position and/or orientation. Furthermore, the program may determine whether the tissue depth to the implant 108 will allow for effective telemetry. The program may also determine proper alignment with adjacent-level implants 108. Having determined a location and orientation where there is available space and where telemetry is likely to be effective, the planning program may guide the surgeon during installation of the actual implant 108 and/or install the implant 108 using a robotic arm or other manipulator. That is, the trial-fitting process is shown on a display of a computer system, such as a surgical-planning system. This virtual trial fitting provides detail of fitment to the subject's anatomy and provides telemetry depth confirmation. In some examples, the virtual trial may be optionally displayed on a tool used to install bone screws to guide installation of a bone screw.

Figure 5:
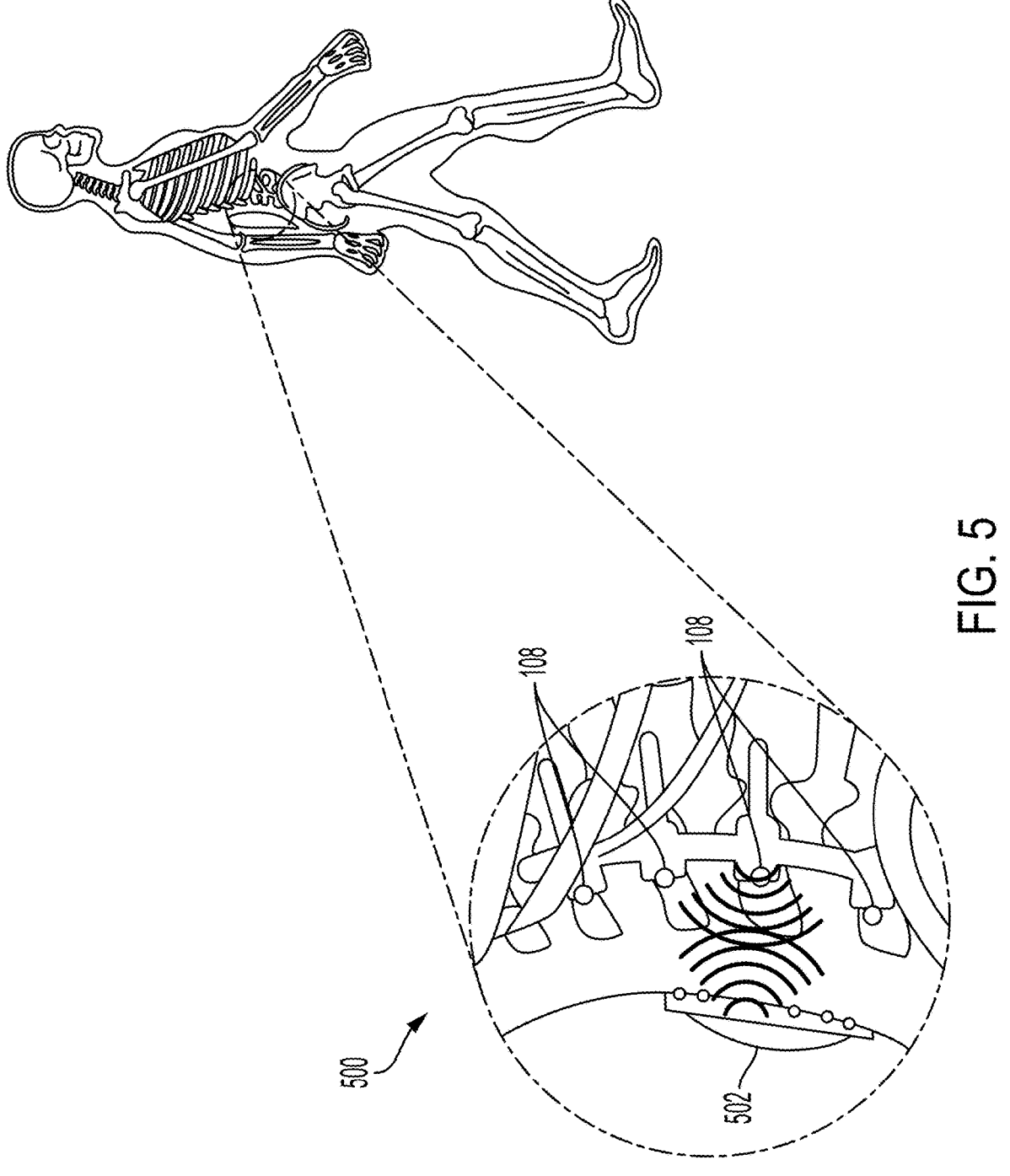
FIG. 5 illustrates an example of a surgical site monitoring system according to an embodiment.

FIG. 5 illustrates an example of a surgical site (SS) monitoring system 500 that may utilize example implants 108 disclosed herein. In some embodiments, the SS monitoring system 500 may be a surgical site load monitoring system (using one or more strain gauges) and/or an infection monitoring system (using one or more temperature sensors). FIG. 5 illustrates a spinal-fusion construct having multiple separate sensor-equipped implants 108, each of which may have one or more sensors. Other embodiments within the scope of this disclosure include multiple implant systems, e.g., multiple spinal-fusion constructs, or one spinal-fusion construct and a separate sensor-equipped implant 108. Other combinations and permutations of implant systems and/or sensor-equipped implants 108 are also within the scope of the disclosure.

In one or more embodiments, the SS monitoring system 500 includes an external reader device 502 configured to receive sensor data from the implants 108. For the embodiments in which the SS monitoring system 500 includes an array of implants 108 having various MEMs sensors, the received data from the one or more MEMs sensors may be compared to one another to diagnose the quality of the surgical procedure, the integrity of the implant 108, and/or an infection at the surgical site.

Embodiments have been described in this document with the aid of functional building blocks illustrating the implementation of specified functions and relationships. The boundaries of these functional building blocks have been arbitrarily defined in this document for the convenience of the description. Alternate boundaries can be defined as long as the specified functions and relationships (or their equivalents) are appropriately performed. Also, alternative embodiments can perform functional blocks, steps, operations, methods, etc. using orderings different than those described in in this document.

The features from different embodiments disclosed herein may be freely combined. For example, one or more features from a method embodiment may be combined with any of the system or product embodiments. Similarly, features from a system or product embodiment may be combined with any of the method embodiments herein disclosed.

References in this document to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Furthermore, when a particular feature, structure, or characteristic is described in connection with an embodiment, it would be within the knowledge of persons skilled in the relevant art(s) to incorporate such feature, structure, or characteristic into other embodiments whether or not explicitly mentioned or described in this document. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but still co-operate or interact with each other.

The breadth and scope of this disclosure should not be limited by any of the above-described example embodiments but should be defined only in accordance with the following claims and their equivalents.

The invention claimed is:

1. A trial fitting device for a smart implant, the device comprising:
   a handle;
   a shaft extending from the handle;
   a head portion attached to the shaft such that the head portion rotates with the shaft;
   a transmitter disposed in the head portion, the transmitter configured to transmit a test signal;
   a rotational indicator disposed on the shaft and/or the handle, the rotational indicator configured to indicate a rotational orientation of the head portion; and
   a telemetry gauge disposed on the shaft and/or the handle, the telemetry gauge configured to indicate a threshold distance from the head portion.

2. The trial fitting device of claim 1, wherein the head portion is shaped and dimensioned to correspond with a smart implant.

3. The trial fitting device of claim 2, wherein the head portion includes a visual cue of where a longitudinal rod would interface with the smart implant.

4. The trial fitting device of claim 1, wherein the telemetry gauge is configured to indicate a depth of tissue that permits effective telemetry from a smart implant in the position and orientation of the head portion.

5. The trial fitting device of claim 4, wherein the telemetry gauge is configured to indicate a range of distances indicating a range of tissue depths that permit effective telemetry, the range of distances based on a parameter of the tissue.

6. The trial fitting device of claim 1, further comprising a control configured to cause the transmitter to transmit the test signal.

7. The trial fitting device of claim 1, wherein the transmitter is configured to transmit the test signal at one of at least two different strengths.

8. The trial fitting device of claim 1, wherein the handle and the shaft share a longitudinal axis.

9. The trial fitting device of claim 1, wherein the handle comprises an ergonomic grip.

10. The trial fitting device of claim 1, wherein the rotational indicator is etched into the handle.

11. The trial fitting device of claim 1, wherein the head portion is shaped and dimensioned to correspond with an interbody device.

12. A method of trial-fitting an implant, the method comprising:
   receiving a trial-fitting tool comprising:
      a handle;
      a shaft extending from the handle;
      a head portion attached to the shaft such that the head portion rotates with the shaft, the head portion shaped and dimensioned to correspond with a smart implant;
      a rotational indicator disposed on the shaft and/or the handle, the rotational indicator configured to indicate a rotational orientation of the head portion; and
      a telemetry gauge disposed on the shaft and/or the handle, the telemetry gauge configured to indicate a threshold distance from the head portion;

using the handle of the trial-fitting tool to:

position the head portion at a trial location for an implant; and adjust, as needed, the position and orientation of the head portion to fit available space;

confirming, using the rotational indicator, that the head portion has a desired orientation;

confirming, using the telemetry gauge, that a point of incision is within the threshold distance from the head portion to the point of incision; and installing the implant in place of the trial-fitting tool.

13. The method of claim 12, further comprising, in response to the head portion not fitting at the trial location, using a trial-fitting tool having a second head portion, the second head portion shaped and dimensioned to correspond with a second smart implant, to position the second head portion at the trial location.

14. The method of claim 13, wherein using the trial-fitting tool having the second head portion comprises replacing the head portion of the trial-fitting tool with the second head portion.

15. The method of claim 12, wherein:

the trial-fitting tool further comprises a transmitter disposed in the head portion and configured to transmit a test signal; and the method further comprises, while the head portion is positioned at the trial location, causing the transmitter to transmit the test signal.

16. The method of claim 12, wherein:

the method further comprises assessing attenuation characteristics of the tissue between the head portion and the telemetry gauge; and confirming that the point of incision is within the threshold distance is based on the assessed attenuation characteristics.

17. The method of claim 12, wherein positioning the head portion at the trial location comprises positioning the head portion by a surgical navigation robot.

18. A trial fitting device for a smart implant, the device comprising:

a handle;

a shaft extending from the handle;

a head portion attached to the shaft such that the head portion rotates with the shaft, wherein the head portion includes a visual cue of where a longitudinal rod would interface with the smart implant;

a rotational indicator disposed on the shaft and/or the handle, the rotational indicator configured to indicate a rotational orientation of the head portion; and a telemetry gauge disposed on the shaft and/or the handle, the telemetry gauge configured to indicate a threshold distance from the head portion.

19. The trial fitting device of claim 18, wherein the telemetry gauge is configured to indicate a depth of tissue that permits effective telemetry from a smart implant in the position and orientation of the head portion.

20. The trial fitting device of claim 18, wherein the rotational indicator is etched into the handle.

\* \* \* \* \*